United States Patent [19]

Titcomb et al.

[11] Patent Number: 6,004,512
[45] Date of Patent: *Dec. 21, 1999

[54] SAMPLE CARTRIDGE SLIDE BLOCK

[75] Inventors: Paul Titcomb, Sagamore; Michael J. Finney, Cambridge; David Cohen, West Roxbury, all of Mass.

[73] Assignee: MJ Research, Waltham, Mass.

[ * ] Notice: This patent issued on a continued prosecution application filed under 37 CFR 1.53(d), and is subject to the twenty year patent term provisions of 35 U.S.C. 154(a)(2).

[21] Appl. No.: 08/567,887

[22] Filed: Dec. 8, 1995

[51] Int. Cl.$^6$ .............................. G01N 21/00; C12M 1/38
[52] U.S. Cl. .............................. 422/63; 422/104; 436/43; 436/183; 435/303.1; 219/520; 219/521
[58] Field of Search .............................. 422/67, 63, 104; 435/287, 290, 316, 809, 303.1; 436/43, 50, 183, 47, 809; 62/3.2; 219/520, 521, 525, 526

[56] References Cited

U.S. PATENT DOCUMENTS

| | | | |
|---|---|---|---|
| 3,035,416 | 5/1962 | Wagner | 62/3 |
| 3,192,727 | 7/1965 | Ashby et al. | 62/3 |
| 3,348,418 | 10/1967 | Utting et al. | 73/421 |
| 3,562,114 | 2/1971 | Steidl et al. | 195/139 |
| 3,684,452 | 8/1972 | Bessman | 422/64 |
| 4,315,300 | 2/1982 | Parmerlee et al. | 361/382 |
| 4,609,037 | 9/1986 | Wheeler et al. | 165/61 |
| 4,629,862 | 12/1986 | Kitagawa et al. | 219/200 |
| 4,727,032 | 2/1988 | Baisch et al. | 436/47 |
| 4,777,561 | 10/1988 | Murphy et al. | 361/385 |
| 4,865,986 | 9/1989 | Coy et al. | 435/290 |
| 5,038,852 | 8/1991 | Johnson et al. | 165/12 |
| 5,090,617 | 2/1992 | Swan et al. | 236/3 |
| 5,133,937 | 7/1992 | Frackleton et al. | 422/81 |
| 5,149,654 | 9/1992 | Gross et al. | 435/287 |
| 5,224,536 | 7/1993 | Eigen et al. | 165/32 |
| 5,255,520 | 10/1993 | O'Geary et al. | 62/3.2 |
| 5,333,675 | 8/1994 | Mullis et al. | 165/12 |
| 5,410,130 | 4/1995 | Braunstein | 219/521 |
| 5,430,957 | 7/1995 | Eigen et al. | 34/423 |
| 5,446,263 | 8/1995 | Eigen et al. | 219/521 |

FOREIGN PATENT DOCUMENTS

| | | |
|---|---|---|
| 0611598 | 8/1994 | European Pat. Off. . |
| 0647707 | 12/1995 | European Pat. Off. . |
| WO93/09486 | 5/1993 | WIPO . |
| WO94/23326 | 10/1994 | WIPO . |
| WO95/10035 | 4/1995 | WIPO . |

*Primary Examiner*—Long V. Le
*Attorney, Agent, or Firm*—Mintz, Levin, Cohn, Ferris, Glovsky and Popeo

[57] ABSTRACT

A sample cartridge block that includes a first plate, a second plate and a third plate. The third plate is thermally connected to the first plate and the second plate. In some embodiments, the block is capable of holding a relatively high density of sample cartridges. In certain embodiments, the block provides good sample temperature stability while the sample temperature is held constant or while the sample temperature is being changed. According to the invention, a sample block may include one material or more than one material. Preferably, a sample cartridge block has a relatively low thermal mass. In some embodiments, the first plate of a sample cartridge block may have a larger surface area than the surface area of the third plate. According to the present invention, the first plate of the sample cartridge block may be thermally connected to a temperature controller. In certain embodiments, a sample cartridge block may have a relatively large surface area in contact with a temperature controller.

6 Claims, 8 Drawing Sheets

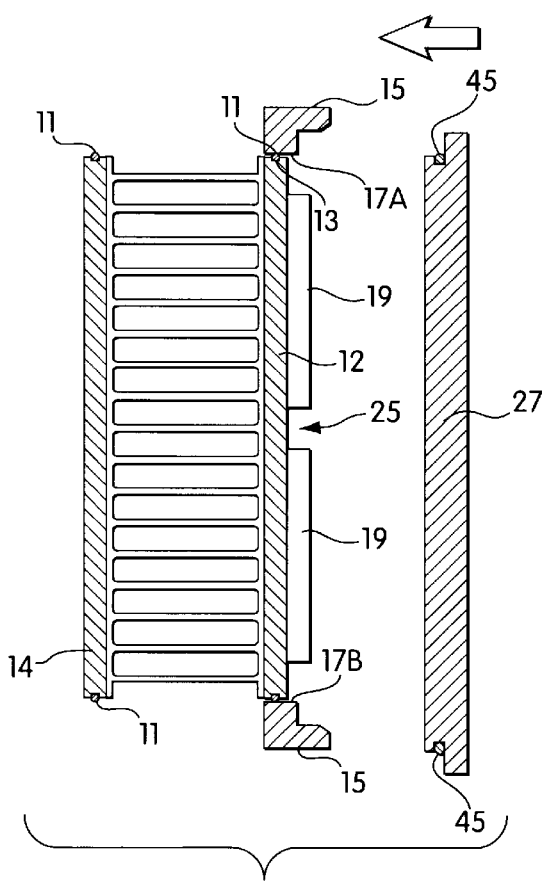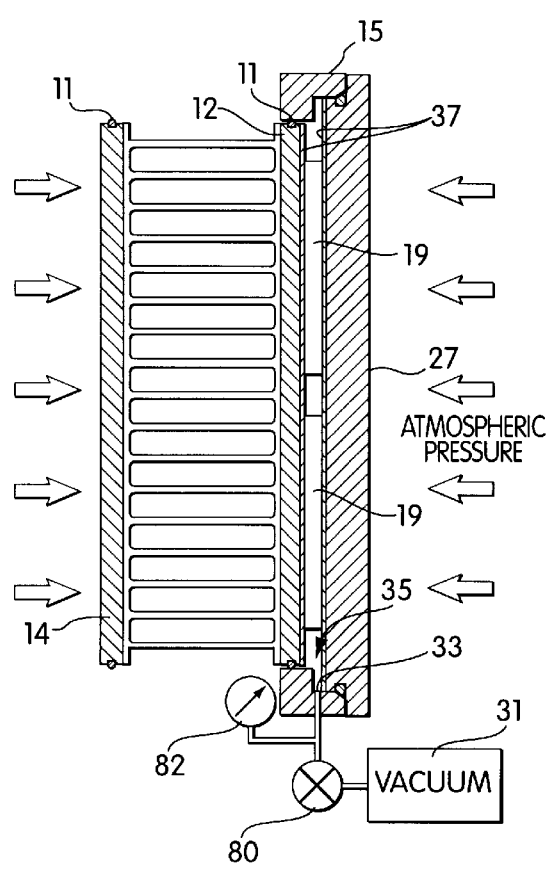

SAMPLE CARTRIDGE SLIDE BLOCK

BACKGROUND OF THE INVENTION

1. Field of the Invention

The present invention relates generally to sample cartridge blocks and more specifically to such blocks which are capable of providing improved sample temperature characteristics and increased sample density.

2. Discussion of the Related Art

A variety of biochemical experiments, involve monitoring certain temperature sensitive reactions. Typically, such studies include thermal cycling of the sample. Such experiments include: nucleic acid hybridizations, polymerase chain reaction (PCR) and its variants (e.g., RT-PCR), isothermal amplification techniques (e.g., "NASBA", "In-Situ-3SR", "PRINS"), cycling "PRINS" and antigen based detection of tissue features. These procedures and general background are contained in the following literature references: *Current Protocols in Molecular Biology*, F. M. Ausubel, et al., eds., John Wiley & Sons, Inc. Sections 14.3 and 14.7; *Current Protocols in Molecular Biology*, F. M. Ausubel, et al., eds., John Wiley & Sons, Inc., Section 14.8; Steacker, H., M. Cammer, R. Rubenstein and T. R. Van de Water. 1994. A procedure for RT-PCR Amplification of mRNAs on Histological Specimens. *BioTechniques*. 16:76–80; Sooknanan, R. And L. T. Malek. 1995. NASBA. A detection and amplification system uniquely suited for RNA. *Bio/Technology*. 13:563–564; Zehba, I., G. W. Hacker, J. F. Sallstrom, E. Rylander and E. Wilander. 1992. Self sustained sequence replication-based amplification (3SF) for the in situ detection of MRNA in cultured cells. *Cell Vision*. 1:20–24; Gosden, J., D. Hanratty, J. Starling, J. Fantes, A. Mitchell, and D. Porteous. 1991. Oligonucleotide-primed in situ DNA synthesis (PRINS): a method for chromosome mapping, banding and investigation of sequence organization. *Cytogenet. Cell Genet*. 57:100–104; Watkins, S. Immunohistochemistry. in: *Current Protocols in Molecular Biology*, F. M. Ausubel, et al., eds., John Wiley & Sons, Inc., Section 14.6. In such studies, the sample may be rapidly or slowly cycled among a variety of temperatures ranging up to nearly 100° C.

Accordingly, various sample cartridges, such as microscope slides, are used in large volumes in both industry and academia. As a result, studying individual sample cartridges can be both tedious and inefficient. Therefore, sample blocks, devices that are capable of holding several sample cartridges, are often used. To optimize efficiency and economy, it is typically desirable to utilize sample cartridge blocks that are capable of holding or containing a relatively large number of samples and/or sample cartridges.

In a variety of circumstances, it is desirable to use a sample cartridge block that can monitor and control the temperature of a sample cartridge contained within the sample cartridge block. Therefore, sample blocks are typically capable of providing temperature control of the sample cartridges. When using a temperature controller in conjunction with a sample cartridge block, it is often advantageous to minimize temperature gradients throughout the three dimensional volume defined by the sample cartridge block so that the temperature of each sample cartridge contained within the sample cartridge block can be controlled to within some acceptable range of temperatures.

Typically, it is advantageous for a sample cartridge block to be capable of changing the temperature of a sample or sample cartridge at a relatively high rate while maintaining a relatively low thermal gradient throughout the sample cartridge block. To achieve this goal, a sample block should preferably include a material that has a relatively high thermal conductance. In order to achieve this goal, it is desirable for the surface area of the sample cartridge block in contact with the temperature controller to be comparatively high.

One known prior art sample cartridge block, designed for the Perkin Elmer Gene Amp In Situ 100 System, includes a horizontal base plate and sample plates which project vertically from the base plate to form a comb-like structure. A spring is located within each slot to hold the sample cartridges in place within the sample block. However, since the sample cartridges are placed vertically within the sample block, special sample cartridges must be used which reduce or eliminate the possibility of sample leakage due to gravity. Moreover, this sample block design allows the temperature of the slides to be controlled from only one side. As a result, asymmetric heating of the samples occurs due to a thermal gradient, and the temperature stability of the samples and/or sample cartridges is limited. Furthermore, this design offers a relatively poor heat pump area to thermal mass ratio, resulting in inefficient heating. Thus, the sample block has a relatively complex design and provides relatively poor sample temperature control characteristics.

Another sample cartridge block, designed for the Hybaid OmniSlide thermal cycler, includes an essentially planar surface and recessions. The recessions are designed to hold sample cartridges in a side-by-side fashion. This arrangement results in a relatively small cartridge density. In addition, precise temperature control of samples and sample cartridges is difficult because the cartridges must be separated by a distance of at least the width of a sample cartridge. Furthermore, the temperature of the sample block is controlled from the undersurface only, and heating occurs by electrical resistance and cooling is achieved by forced air flow. As a result, the sample cartridge block provides comparatively poor sample temperature characteristics. Moreover, with this design, good thermal control of the sample cartridges would require a separate sensor and independent temperature control for each sample cartridge. Hence, this sample block provides a relatively low sample density and comparatively poor sample temperature control characteristics.

An additional design for a sample block, the MJ Research PTC-100-16MS, includes a stacked, two-dimensional array of sample cartridge slots machined into a sample block. In addition, a temperature control device is located at the underside of the sample block only, so heat flow across the sample block is asymmetric. Thus, there is usually a temperature gradient across the sample cartridge block. To reduce the temperature gradient across the sample block, a relatively low rate of heating and cooling must be used, but this can reduce the utility of the sample cartridge block. Accordingly, this arrangement provides limited sample temperature control.

Thus, it remains a desirable in the art to provide a sample block having a design that affords high sample cartridge density while avoiding uneven heating of samples and/or sample cartridges due to thermal gradients. It is a further challenge in the art to provide a sample block that allows sample cartridges to be stacked horizontally. Furthermore, it is a general problem to design a sample cartridge block that has good mechanical integrity yet also has a relatively low thermal mass. Typically, low thermal mass materials provide comparatively poor mechanical integrity. Hence, it would be advantageous to provide a sample cartridge block designed to reduce or eliminate the significance of having good mechanical integrity.

SUMMARY OF THE INVENTION

Therefore, it is an object of the present invention to provide a sample block that has a relatively high sample density.

It is another object of the present invention to provide a sample block that is capable of providing a relatively low temperature gradient throughout the three dimensional space that defines the sample block.

It is yet another object of the present invention to provide a sample block that has a relatively low thermal mass.

It is still another object of the present invention to provide a sample cartridge block that has a relatively high heat pump surface area. In certain embodiments, the heat pump area may be planar.

It is a further object of the present invention to provide a sample block that has a relatively high heat pump surface area to thermal mass ratio.

It is yet a further object of the present invention to provide a sample block comprising more than one material.

It is still a further object of the present invention to provide a sample cartridge block that has a temperature controller in contact with at least two surfaces of the sample cartridge block.

In one illustrative embodiment, the present invention comprises an assembly that includes a sample block and a temperature controller. The sample block comprises a first plate, a second plate and a third plate. The third plate is thermally connected to the first plate and the second plate, and the temperature controller is disposed along the outer surface of the first plate.

In another illustrative embodiment, the present invention comprises a sample cartridge block. The block includes a first plate, a second plate and a third plate. The third plate is thermally connected to the surfaces of the first plate and the second plate, and the first plate comprises a different material than the third plate.

In a further illustrative embodiment, the present invention comprises a sample cartridge block. The block includes a first plate, a second plate and a third plate. The third plate is thermally connected to the first plate and the second plate, and the surface area of the first plate is greater than the surface area of the third plate.

In yet a further illustrative embodiment, the present invention comprises a sample cartridge block. The block includes a first plate, a second plate and a plurality of connecting plates. Each connecting plate is thermally connected to the first plate and the second plate, and the block has a sample cartridge density of at least about 5 cartridge per inch in a direction perpendicular to the direction of the connecting plates.

In another illustrative embodiment, the present invention comprises a sample cartridge block. The block includes a first plate, a second plate and a third plate. The third plate is thermally connected to both the first plate and the second plate, and the sample cartridge block has a thermal mass of at most about 53 cal/C.

In some embodiments, it is an advantage of the present invention to provide an assembly which includes a sample cartridge block and is designed to reduce the significance of using materials that have relatively high mechanical strength or structural integrity.

In certain embodiments, it is an advantage of the present invention to provide a sample cartridge plate having at least one connecting plate with a thickness of at most about 30 mils.

BRIEF DESCRIPTION OF THE DRAWINGS

FIG. 7 is a cross-sectional view of an embodiment of yet another stage of construction of an assembly according to the present invention;

FIG. 8 is a cross-sectional view of an embodiment of a further stage of construction of an assembly according to the present invention;

DETAILED DESCRIPTION

Figures 1, 2:
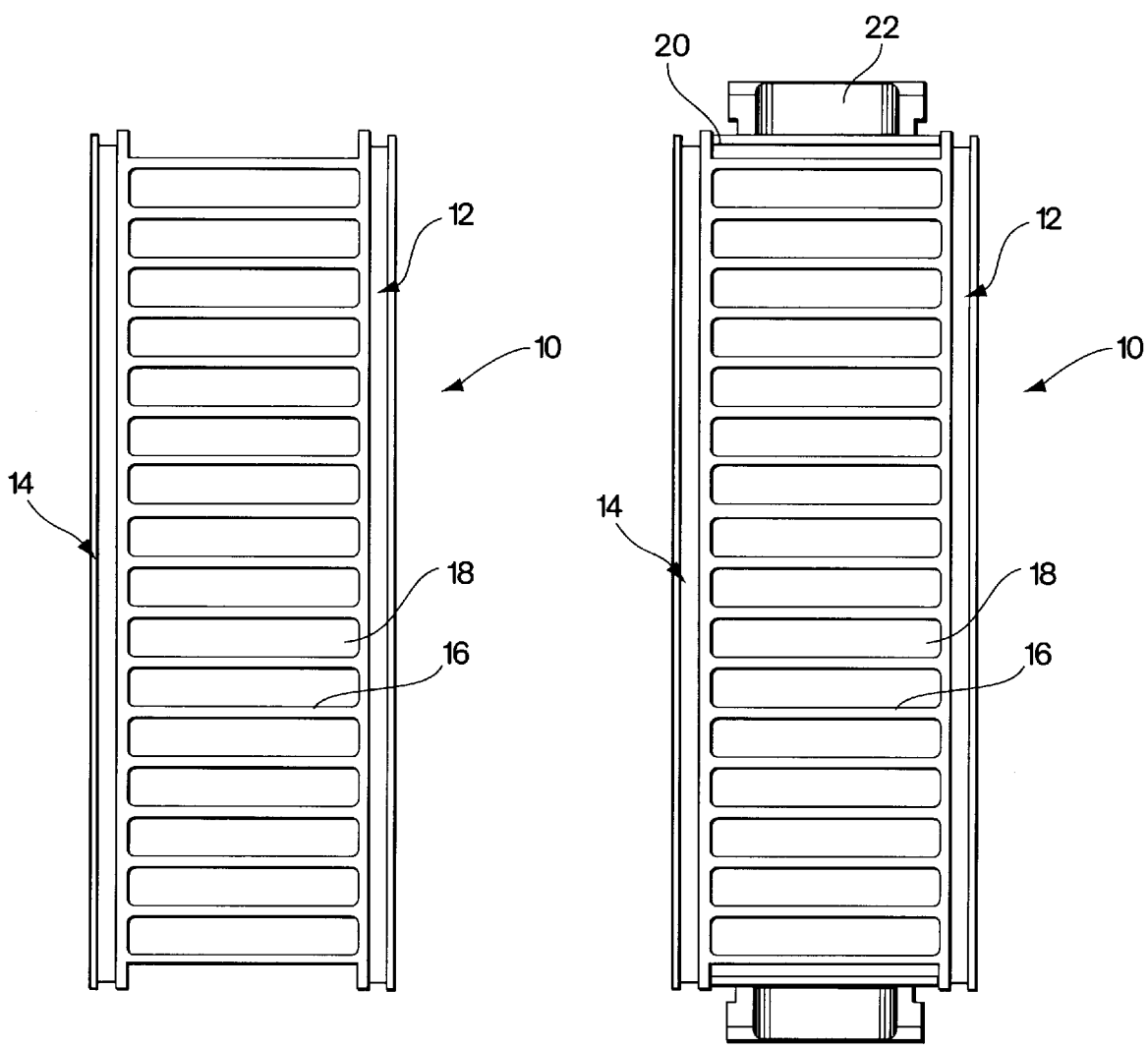
FIG. 1 is a cross-sectional view of one embodiment of a sample cartridge block according to the present invention.
FIG. 2 is a cross-sectional view of another embodiment of a sample cartridge block according to the present invention.

The present invention relates to sample cartridge blocks designed to hold sample cartridges. FIG. 1 shows one embodiment of a sample cartridge block 10 according to the present invention. Block 10 includes a first base plate 12 and a second base plate 14. Connecting plates 16 are connected to both plate 12 and plate 14, and sample cartridge slots 18 are located between neighboring connecting plates 16.

A "sample cartridge" as used herein refers to a device that is capable of holding a sample, such as an aliquot of solution. For example, a sample cartridge may be a single microscope slide, two microscopes slide that are in contact, a microscope slide that is in contact with a cover slip, a sealing device with a gasket glued on, a sealing device with a gasket pressed on or cartridge carrying devices. Typically, a sample cartridge includes at least one microscope slide. "Sample cartridge block" herein denotes an apparatus that is capable of holding or containing at least one sample cartridge. A sample cartridge block may be arranged to hold a sample cartridge vertically, horizontally or both. Usually, a sample cartridge block is designed to hold a sample cartridge horizontally within the sample cartridge block. In certain embodiments, a sample cartridge block may be able to monitor and control the temperature of a sample cartridge and/or a sample placed within the sample cartridge block. Typically, a sample cartridge block can increase, decrease or hold constant the temperature of a sample or sample cartridge placed within the sample cartridge block.

Plates 12, 14 and 16 may each comprise the same or different materials. For embodiments in which plates 12, 14 and 16 comprise the same material, block 10 may comprise any material having a relatively high thermal conductivity. Typically, plates 12, 14 or 16 include aluminum, copper or silver. As described herein, in some of these embodiments, plates 12, 14 or 16 may be in contact with an electrically conductive surface, and, for these embodiments, it may be advantageous to have an electrically insulating layer or coating placed around at least a portion of the exterior surface of plates 12, 14 or 16. For example, if aluminum is used, an anodized coating (i.e., aluminum oxide coating) may be used. Alternatively, if silver is used, a coating of aluminum oxide may be plasma sprayed onto at least a portion of the exterior surface of plates 12, 14 or 16. Preferably, plates 12, 14 and 16 include aluminum, more preferably aluminum 6061.

For embodiments in which plates 12, 14 and 16 comprise different materials, plates 12 or 14 may include any material having a relatively high thermal conductivity, such as aluminum, copper or silver. If plates 12 or 14 are to be contacted with an electrically conductive surface, plates 12 or 14 preferably have an electrically insulative coating disposed thereover as described herein. Plate 16 may include a sandwich-like structure of more than one material. For example, plate 16 may include an interior portion of aluminum 6951 having a coating of aluminum 4343 disposed thereover. Alternatively, plate 16 may include a layer of pyrolitic graphite sandwiched between two layers of aluminum.

While certain materials appropriate for use with the present invention have been disclosed herein, it is to be understood that other materials may also be used. Such materials are limited only that they should provide certain advantageous features of the present invention as described herein. Such materials will be obvious to those of ordinary skill in the art.

Plates 12 and 14 may be of any shape so long as sample cartridge block 10 can hold sample cartridges while providing certain advantages of the present invention. For example plates 12 and 14 may have surfaces that are substantially flat (i.e., planar), substantially convex or substantially concave. Preferably, plates 12 and 14 have surfaces that are substantially planar.

Plates 12 and 14 may be arranged at any angle with respect to each other so long as block 10 is capable of holding or containing sample cartridges while providing certain advantageous properties of the present invention. In a preferred embodiment, plates 12 and 14 are substantially parallel.

Connecting plates 16 may have surfaces of any shape so long as block 10 is capable of holding sample cartridges while providing certain advantages of the present invention. For example, connecting plates 16 may have surfaces that are substantially convex, substantially concave or substantially flat (i.e., planar).

Connecting plates 16 may be thermally connected to plates 12 and 14 such that cartridge slots 18 can have any shape so long as block 10 is capable of holding sample cartridges while providing certain advantageous properties of the present invention. For example, cartridge slots 18 may have a cross-sectional shape that is substantially square or rectangular.

Connecting plates 16 may be disposed at any angle with respect to plate 12 or plate 14 so long as sample cartridge block 10 can hold or contain sample cartridges while providing certain advantageous properties of the present invention. For example, connecting plates 16 may be perpendicular to plate 12 or plate 14. In a preferred embodiment, connecting plates 16 are substantially perpendicular to both plates 12 and 14.

According to the present invention, block 10 can provide a high density of sample cartridges by having an increased density of connecting plates 16. A "density of connecting plates" as used herein denotes the number of connecting plates 16 per millimeter as measured in a direction substantially perpendicular to connecting plates 16. The density of connecting plates usually depends upon the thickness of the sample cartridges to be used with sample cartridge block 10. For example, when a microscope slide having a thickness of 1 millimeter is used, block 10 may have a density of cartridge slots of at least about 0.1 connecting plates per millimeter. When using a 1 millimeter thick cartridge plate, block 10 preferably has a density of cartridge slots of at least about 0.2 connecting plates per millimeter, more preferably at least about 0.3 connecting plates per millimeter and most preferably at least about 0.4 connecting per millimeter.

Often the density of connecting plates 16 can be increased by decreasing the thickness of plates 16. In addition, the thickness of a plate 16 may depend upon the distance between plates 12 and 14 since plate 16 may be used to provide both mechanical integrity to block 10 and to provide thermal conductance between plates 12 or 14 and a sample cartridge. As the distance between plates 12 and 14 increases, the thickness of plate 16 may be increased to provide increased mechanical support. Alternatively, as the distance between plates 12 and 14 decreases, the thickness of plate 16 may be decreased. Furthermore, in order to provide good thermal conduction between plates 12 or 14 and the center point of plate 16, plate 16 may need to have an increased thickness as the thickness between plates 12 and 14 is increased. Therefore, in some embodiments when plate 12 is spaced about 25 millimeters from plate 14, a connecting plate 16 preferably has a thickness of at most about 50 mils, more preferably at most about 40 mils and most preferably at most about 30 mils.

In certain embodiments, block 10 has a decreased maximum temperature variation. "Maximum temperature variation" herein denotes the change in temperature from a first point within block 10 to second point within the volume in which sample cartridges are held within block 10 as measured between the first point and the second point. Preferably, the maximum temperature variation of block 10 is at most about 1 C, more preferably at most about 0.7 C and most preferably at most about 0.5 C (i.e, preferably a change in temperature between the first point and the second point of +/−0.5 C, more preferably +/−0.35 C and most preferably +/−0.25 C).

Sample cartridge block 10 may be capable of maintaining a relatively low maximum temperature variation subsequent to undergoing a temperature change. In one embodiment, block 10 preferably has a maximum temperature variation of at most about 1° C. (i.e., a change in temperature between the first point and the second point of +/−0.5° C.) about 30 seconds after stopping a temperature change of at least about 1° C. per second, more preferably at least about 2° C. per second and most preferably at least about 3° C. per second. In another embodiment, block 10 preferably may be capable of having a maximum temperature variation of at most about 0.7° C. (i.e., a change in temperature between the first point in the second point of +/−0.35° C.) about 25 seconds after a change in temperature of at least about 1° C. per second, more preferably at least about 2° C. per second and most preferably at least about 3° C. per second. In a further embodiment, block 10 preferably may be capable of having a maximum temperature variation of at most about 0.5° C. (i.e., a change in temperature between the first point and the second point of +/−0.25° C.) 15 seconds after undergoing a change in temperature of at least about 1° C. per second, more preferably at least about 2° C. per second and most preferably at least about 3° C. per second.

According to the present invention, sample cartridge block 10 may have a decreased thermal mass. "Thermal mass" herein refers to the mathematical product of the gravimetric mass of a material and the specific heat of the material. The "specific heat" as used herein refers to the amount of heat required to raise the temperature of one gram material 1° C. Preferably, block 10 has a thermal mass of at most about 53 cal/° C., more preferably at most about 40 cal/° C. and most preferably at most about 30 cal/° C.

For certain embodiments, block 10 may be comprised of a material having a low specific heat (which relates to a high thermal conductivity) so that block 10 has a low thermal mass. For such embodiments, block 10 preferably includes a material having a thermal conductivity of at least about 200 W/m C.

To obtain a low thermal mass, block 10 may include a material having a low gravimetric mass. For example, in certain embodiments, if block 10 comprises aluminum, the gravimetric mass of block 10 is preferably at most about 250 grams, more preferably at most about 200 grams and most preferably at most about 150 grams. In one embodiment, block 10 has a gravimetric mass of about 250 grams. It is to be understood that the gravimetric mass of block 10 is not limiting and that the gravimetric mass of block 10 may have any value so long as block 10 provides certain advantages according to the present invention.

To decrease the thermal mass of sample cartridge block 10, plate 12 and/or plate 14 may have a reduced thickness. For such embodiments, plate 12 and/or plate 14 may have any thickness greater than or equal to the thickness of plate 16. Preferably, plates 12 and/or 14 have a thickness of at most about 0.5 inches, more preferably at most about 0.1 inches and most preferably at most about 50 mils.

In certain embodiments, the present invention may have a relatively high heat pump area. A "heat pump area" as used herein denotes the area of sample cartridge block 10 that is thermally connected to a temperature controller (described below). "Thermally connected" herein denotes a connection between two or more elements that allow the elements to exchange heat. Such a connection may include direct contact or contact through a thermally conductive material, such as a metal. Accordingly, in certain embodiments, block 10 preferably has a heat pump area of at least about 80 square cm, more preferably at least about 100 square cm and most preferably at least about 120 square cm. In one embodiment, block 10 has a heat pump area of about 112 square cm. For some embodiments, the heat pump area of block 10 may be planar (i.e., the surface of the heat pump area of block 10 is substantially in only one plane). However, it is to be understood that the shape, size and heat pump area of block 10 are not limited to particular values disclosed herein, and these parameters are limited only in that block 10 provide certain advantages of the present invention.

According to the present invention, block 10 may have a high heat pump surface area to thermal mass ratio. Preferably, the ratio of the heat pump area of block 10 to the thermal mass of block 10 is at least about 1.5 square cm-C/cal, more preferably at least about 2.5 square cm-C/cal and most preferably at least about 4 square cm-C/cal. In one embodiment, block 10 has a ratio of heat pump area to thermal mass of about 2 square cm-cal/C.

Sample cartridge block 10 may further include at least one device that is capable of allowing block 10 to be thermally connected to certain external devices that are appropriate to use with block 10, such as temperature controllers or heat sinks. Such thermal connection may be achieved by connecting block 10 and the external device to a fastening apparatus.

Figure 3:
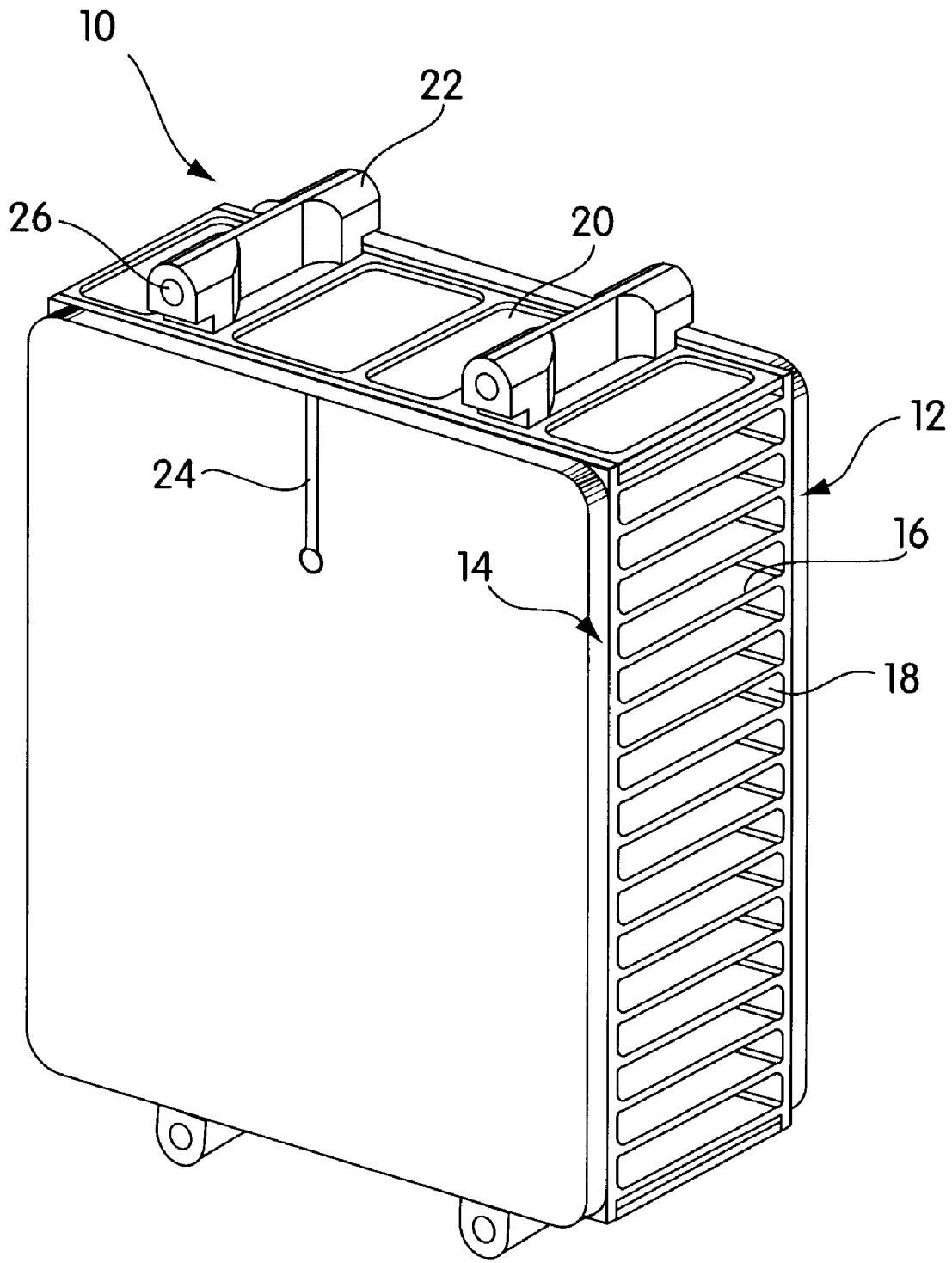
FIG. 3 is a perspective view of a sample cartridge block according to FIG. 2.

Such a fastening apparatus is shown in FIGS. 2 and 3 which depict an embodiment of the present invention in which sample cartridge block 10 includes a heat shield plate 20, an ear attachment 22 and an orifice 24 for a temperature sensor. Heat shield 20 may have any design so long as it is capable of reducing or preventing the flow of heat between ear attachment 22 and plates 12, 14 or 16. Heat shield plate 20 may comprise the same material as plates 12, 14 or 16. Alternatively, heat shield 20 may include a different material from plates 12, 14 or 16. Preferably, heat shield 20 comprises a material having a thermal conductance in a range between about 0.01 W/m C and 1 W/m C. An exemplary and nonlimiting list of such materials includes high heat resistance materials such as plastic, including phenolic plastics.

Ear attachment 22 includes a hole 26 which passes entirely therethrough. Preferably, such a hole is in a direction substantially perpendicular to the surface of plates 12 and 14 along which connecting plates 16 are thermally connected. Ear attachment 22 may have any shape or design so long as it is capable of allowing an external device, such as a temperature controller and/or heat sink, to be thermally connected to sample cartridge block 10. It is to be noted that, as depicted in FIG. 2, ear attachment 22 is not directly connected to plates 12, 14 or 16. Instead, ear attachment 22 is removed from these surfaces so that block 10 may have an increased heat pump surface area as described herein. Ear attachment 22 may comprise the same material as block 10 or heat shield 22. Alternatively, heat shield 22 may comprise a different material from block 10 or a different material from shield 22. In one embodiment, heat shield 22 may comprise a plastic material and ear attachment may comprise a metal.

Temperature sensor 24 is thermally connected to block 10. Temperature sensor 24 may comprise a thermistor, a thermocouple, an integrated circuit sensor or any other sensor capable of sensing temperature. Typically, sensor 24 is a thermistor.

Figure 4:
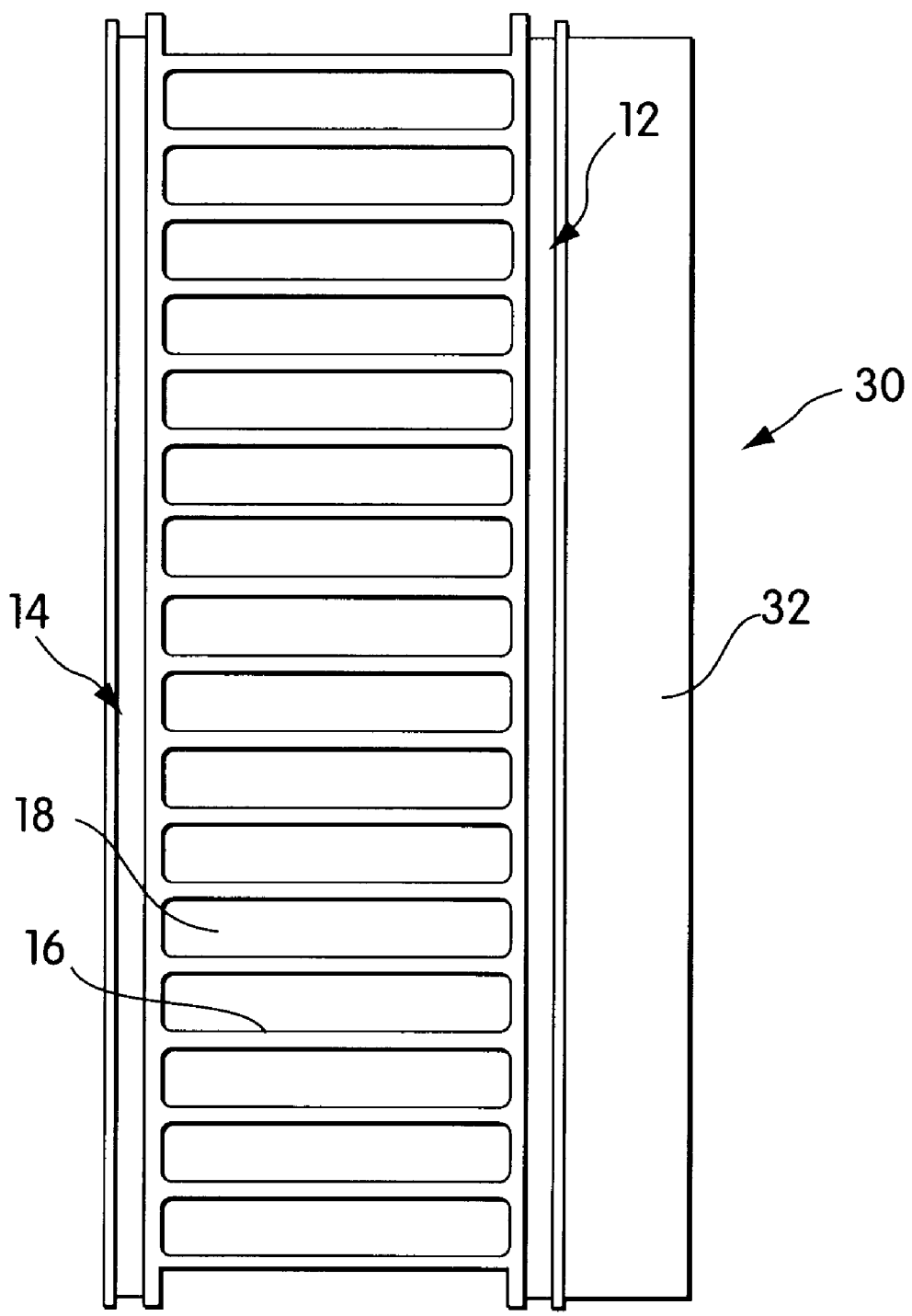
FIG. 4 is a cross-sectional view of one embodiment of an assembly including a sample cartridge block and one temperature controller according to the present invention.

FIG. 4 depicts an embodiment of an assembly 30 according to the present invention in which a temperature controller 32 is thermally connected to the surface of plate 12 of sample cartridge block 10. Temperature controller 32 may comprise any device that is capable of controlling the temperature of samples and or sample cartridges held or contained within sample cartridge block 10. Such devices may include resistive heating circuits, liquid cooling circuits, mechanical refrigeration circuits or solid state heating devices. It is to be noted that, for certain temperature controllers, block 10 may have a relatively complex design. For example, if temperature controller 32 includes a liquid cooling circuit, this liquid cooling circuit may run along the surfaces of plates 12, 14 and 16. Typically, temperature controller 32 comprises a solid state device such as a thermoelectric heat pump module. In one embodiment, temperature controller 32 comprises a Model M1-2009-1 thermoelectric heat pump module from Marlow Industries located in Dallas, Tex. It is to be noted that, in certain embodiments it may be advantageous that plate 12 have a substantially planar surface if temperature controller 32 includes a Model M1-2009-1 heat pump.

Temperature controller 32 may be connected to sample cartridge block 10 in any fashion so long as assembly 30 offers certain advantageous properties of the present invention. Such a connection may include a thermal conduit, such as a piece of metal, that is fastened or contacted with both block 10 and controller 32. Alternatively, block 10 may be in direct physical contact with temperature controller 32. Preferably, a temperature controller 32 appropriate for use with the present invention comprises a Model M1-2009-1 heat pump that is in direct physical contact with the surface of plate 12.

Figure 5:
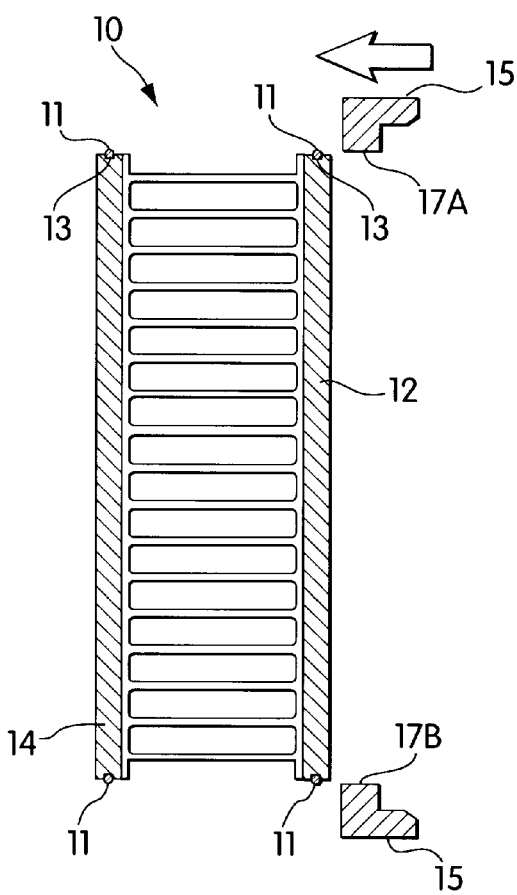
FIG. 5 is a cross-sectional view of an embodiment of one stage of construction of an assembly according to the present invention.
Figure 6:
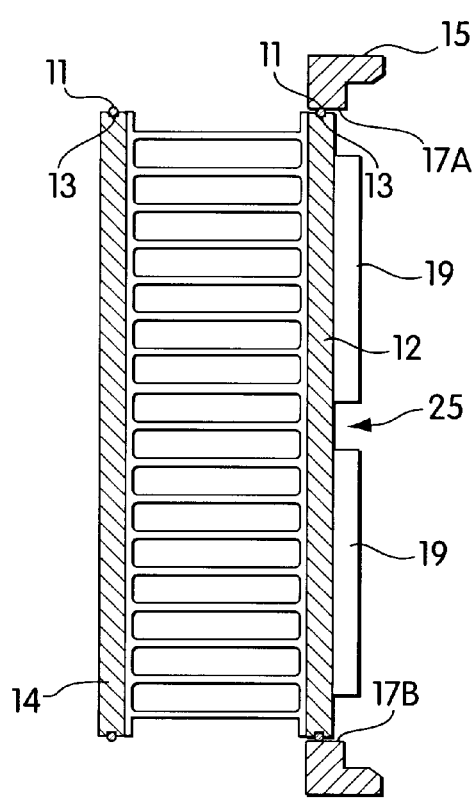
FIG. 6 is a cross-sectional view of an embodiment of another stage of construction of an assembly according to the present invention.
Figure 9:
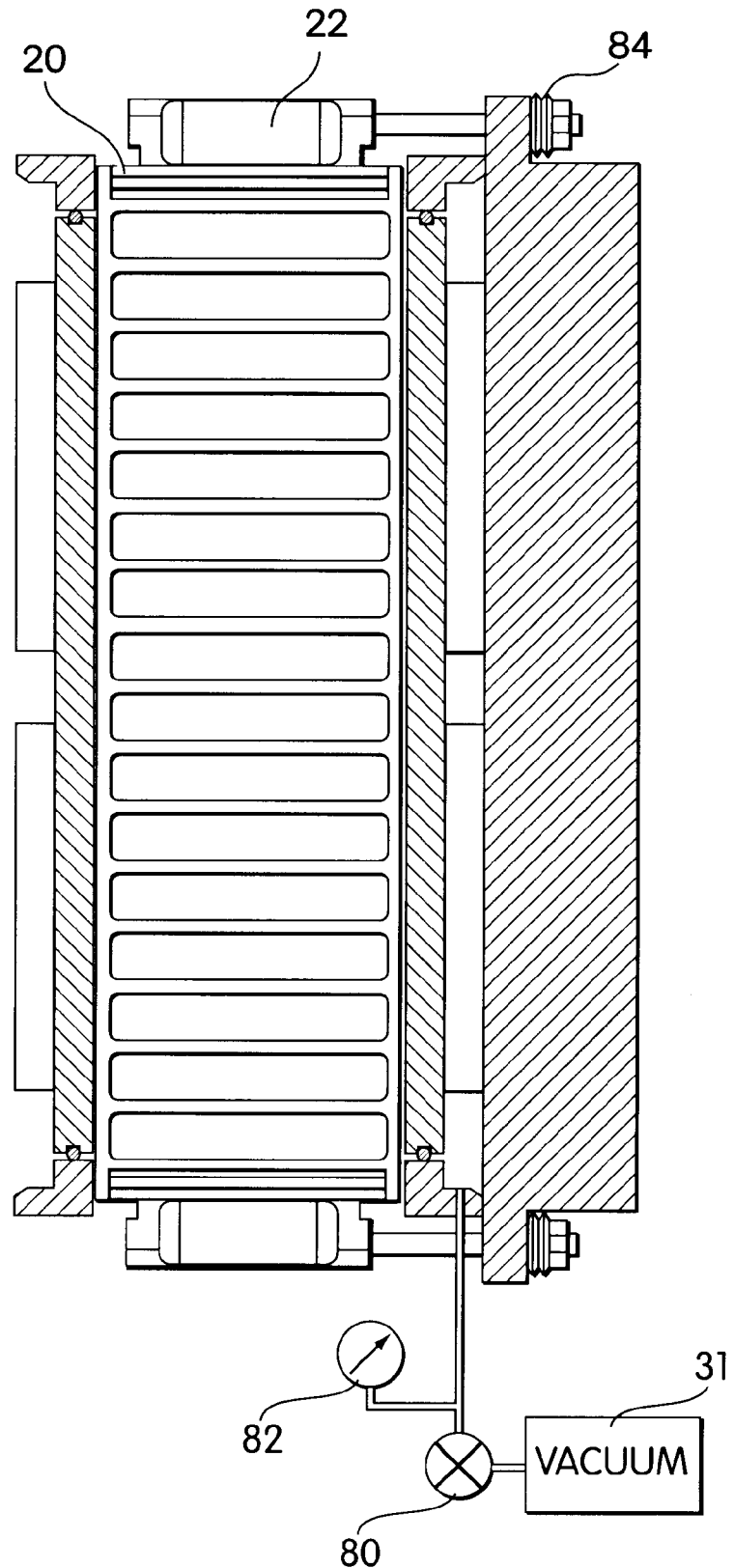
FIG. 9 is a cross-sectional view of an embodiment of yet a further stage of construction of an assembly according to the present invention.

A description of certain aspects of one embodiment of a device assembly is now given (FIGS. 5–10). According to this embodiment, each side of block 10 is constructed independently by methods in accordance with the present invention. Standard O-rings 11 including an appropriate material such as, for example, nitrile, viton or the like, is placed in grooves 13 of plates 12 and 14 (FIG. 5). A retainer 15 is pressed down on plate 12, squeezing o-ring 11 between the edge of block 10 and the inside surface 17A and 17B of retainer 15 (FIG. 6). A temperature controller (including related electronics, senors and the like) 19 is then placed in appropriate positions within a cavity formed by block 10 and central opening 25 of retainer 15.

An O-ring 45 is placed in a corresponding groove in a heatsink 27 and placed against retainer 15. A vacuum source 31 is attached to an opening 33 to the cavity 35 formed by the block 10, heat sink 27 and opening in retainer 15. Atmospheric pressure, acting on the outer surfaces of block 10 and heat sink 27, press heatsink 27 and block 10 together, holding the assembly in compression. In one embodiment, a compression force of about 200 pounds is used. Preferably, this force is evenly distributed across the faces of the heat pump modules. In some embodiments, the heat pump modules are seated into thermal interface sheets 37. Sheets 37 can comprise any material that provides the appropriate compressibility and thermal conductance properties. In certain embodiments, sheets 37 comprise Grafoil TM, from Union Carbide Company, Inc, Cleveland, Ohio 44101. Thermal interface sheets 37 can be placed between block 10 and modules and between modules and heat sink to provide good and uniform thermal heating.

A valve 80 can be used to disconnect the source of vacuum 31 from cavity 35 while maintaining the vacuum within cavity 35. By using a vacuum gauge 82, the functioning of the seals can be tested by observing any change in the vacuum. While holding a vacuum, a belleville washer stack 84 or the like is placed over each post connected to the attachment ears 22 of the block and a threaded fastener used to compress each stack against the outer surface of heat sink. By using belleville washers with a ratio of cone height to thickness (h/t) of close to 1.4, and by compressing each washer to approximately 70% deflection, a change in deflection of +/−0.3 mm (due to assembly tolerance stack errors and dimensional changes caused by thermal cycling) results in a change in applied force of about +/−10%.

The vacuum clamp force allows the belleville washer clamps to be applied (outside the area of the heat pumps) without unbalanced forces being applied to the assembly. Once the belleville washer clamps are set, the vacuum is released and the assembly procedure may be repeated for the opposite side.

Figure 10:
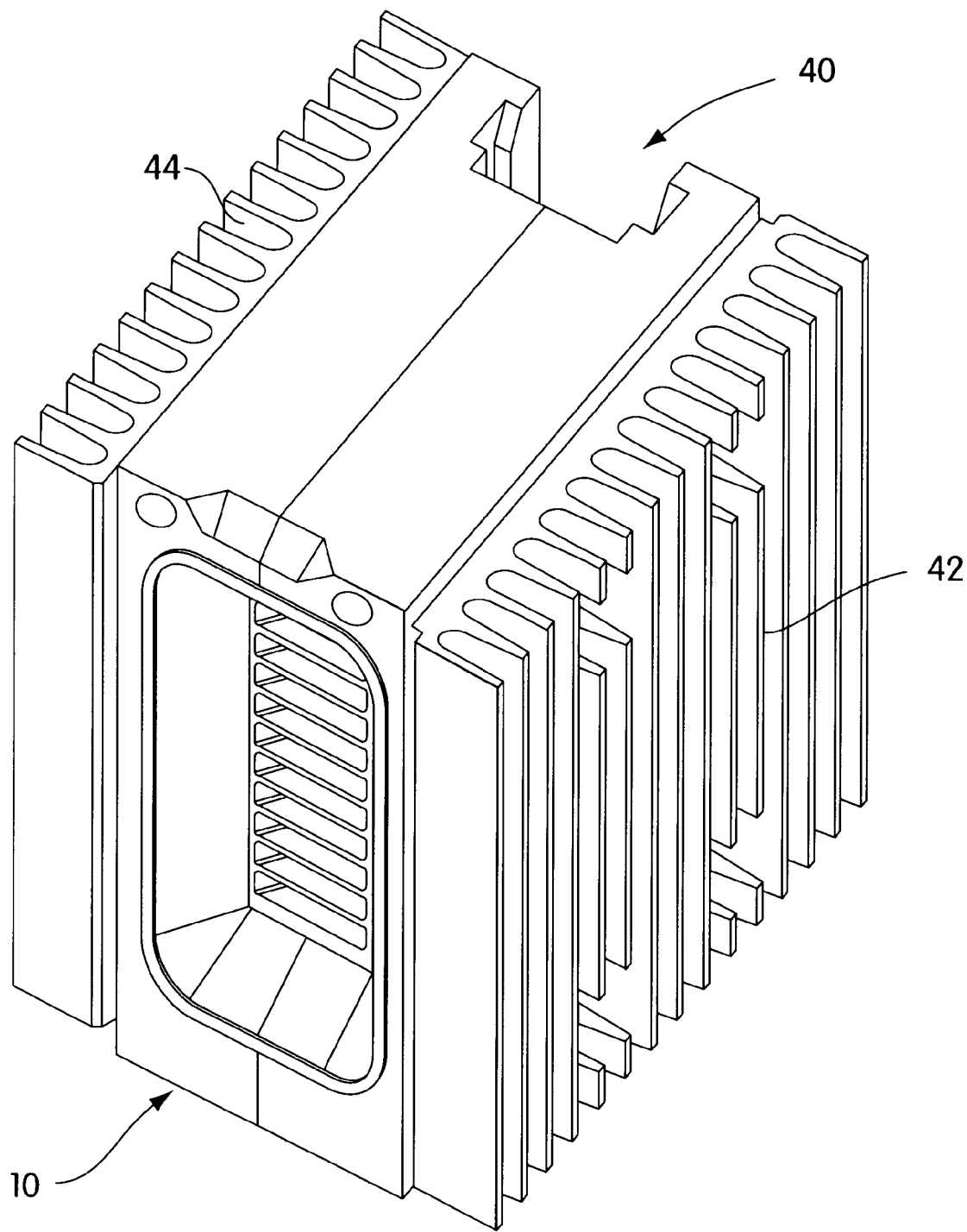
FIG. 10 is a perspective view of an embodiment of an assembly according to the present invention.

FIG. 10 depicts an embodiment of assembly 40 according to the present invention. Assembly 40 includes block 10 and heat sinks 42 and 44.

In certain embodiments, block 10 may be formed from a monolithic portion of material. For such embodiments, electron discharge machining (EDM) processes may be utilized in the formation of block 10. Typically, wire EDM is used in which a traveling wire cuts slots through the material of which block 10 is comprised. The slits so formed are of about the same width as the thickness of the wire. Other processes for providing block 10 from a monolithic portion of material are known to those skilled in the art and are intended to be within the scope of the present invention.

According to the present invention, block 10 may be formed from more than one discrete component. For such embodiments, block 10 may be formed by dip brazing the distinct components together. In this process, the components may be dipped into a molten bath of salt that is at a temperature above the melting point temperature of any interior alloy and below the melting point temperature of any exterior alloy. Prior to exposure to the molten bath, the components may be fit together by machining slots into plates 12 or 14 so that plates 16 can be positioned therein. Dip brazing is often used when block 10 includes aluminum. Alternatively, for certain embodiments, hard or soft soldering may be used to fit the components of block 10 together. Typically, such a soldering process includes silver soldering. This method is often used when block 10 includes copper or silver. The discrete components may be made according to any standard machining techniques, such as milling or sawing. In addition, aluminum extrusion may be used.

Figure 11:
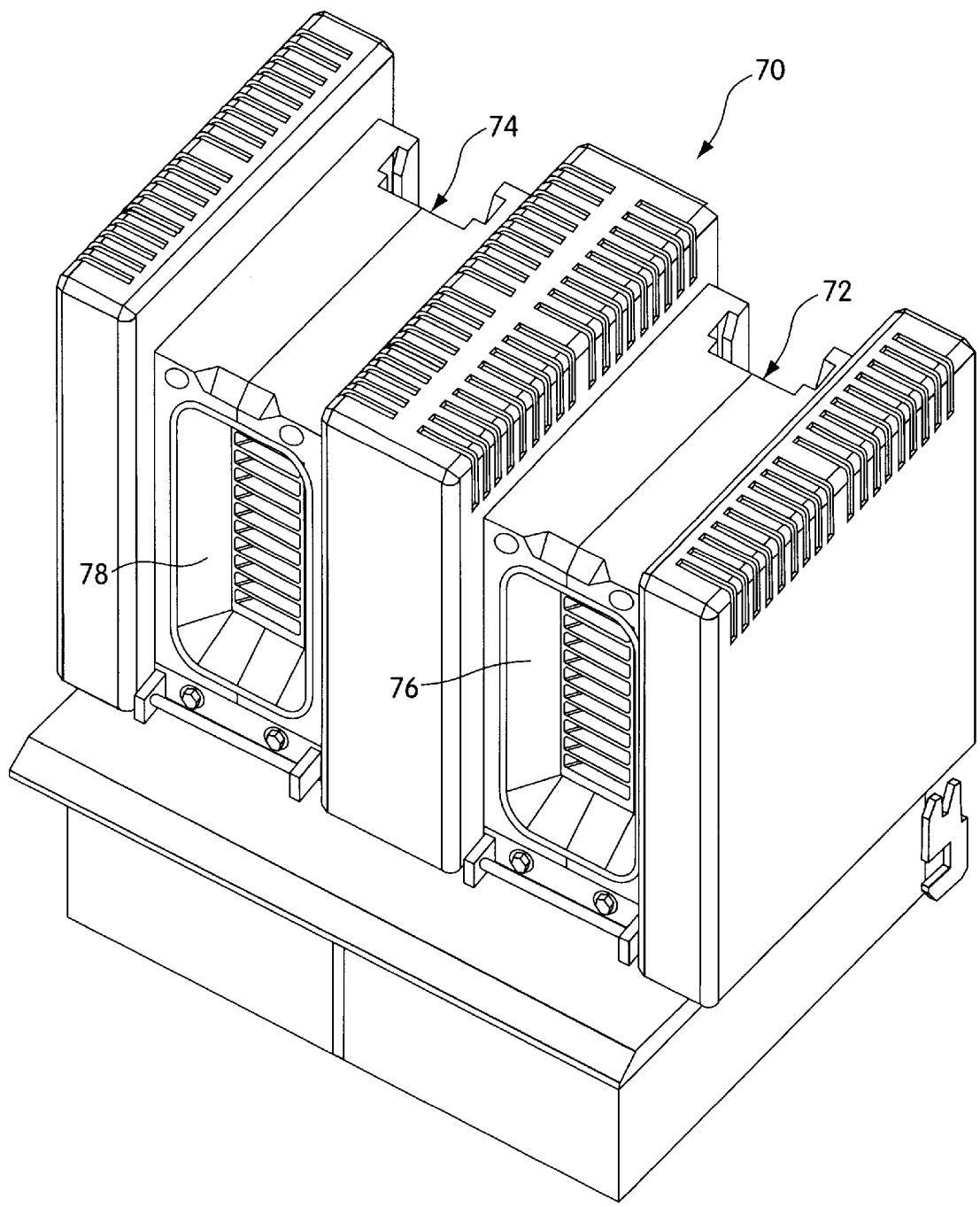
FIG. 11 is a perspective view of an embodiment of a multiassembly including more than one sample cartridge block according to the present invention.

In certain embodiments, more than one assembly (e.g., a multiassembly) including a slide block may be mechanically and/or thermally connected. FIG. 11 depicts an embodiment of a multiassembly 70 according to the present invention which includes assemblies 72 and 74. Assembly 72 includes sample cartridge block 76 and assembly 74 includes sample cartridge block 78.

Having thus described certain embodiments of the present invention, various alterations, modifications and improvements will readily occur to those skilled in the art. Such alterations, modifications and improvements are intended to be part of the disclosure and are intended to be within the scope of the present invention. For example, in some embodiments, a sample cartridge block may include only one sample cartridge slot. In addition, a temperature controller and/or heat sink may be disposed along the surface of a plate of a sample cartridge controller rather than by the use of an car attachment. Moreover, the materials employed, as well as their shapes and dimensions, may be any required. Accordingly, the foregoing description is by way of example only and is not intended as limiting. The invention is limited only as defined in the following claims and equivalents thereto.

What is claimed is:

1. An assembly for holding sample cartridges comprising:
   a sample block, including:
   a first plate having a first surface and a second surface, the second surface being opposite the first surface and the first plate being arranged generally in a vertical orientation;
   a second plate having a third surface and a fourth surface, the fourth surface being opposite the third surface and being generally arranged in a vertical orientation parallel to the first plate;
   a plurality of third plates each having a first end connected to the second surface and a second end connected to a third surface;
   a first temperature controller disposed along the first surface;
   a second temperature controller disposed along the fourth surface;

the plurality of third plates being orientated generally horizontally and perpendicular to the orientation of the first plate and the second plate;

an ear attachment and a heat shield plate, the heat shield plate having a first end and a second end, the ear attachment being thermally connected to the heat shield plate, and wherein the first end of the heat shield plate is thermally connected to the first surface and the second end of the heat shield plate is thermally connected to the third surface; and wherein the sample block is formed of a material having a thermal mass of at most about 53 cal/° C.

2. The assembly according to claim 1 wherein the temperature gradient of the assembly is at most about 0.25° C.

3. The assembly according to claim 2 wherein the assembly has a temperature change rate of at least about 3° C. per second.

4. The assembly according to claim 1 wherein the first and second temperature controllers include a heat pump module.

5. The assembly according to claim 1 further comprising a temperature sensor, the temperature sensor being thermally connected to a plate selected from the group consisting of the first plate, the second plate and the plurality of third plates.

6. The assembly according to claim 1, further comprising a post, a conical washer having an orifice and a heat sink having an orifice, wherein the ear attachment has an orifice and the post is partially disposed within the orifice of the heat sink, the orifice of the conical washer and the orifice of the ear attachment, and wherein the heat sink is disposed along a surface selected from the group consisting of the second surface and the fourth surface.

* * * * *